(12) United States Patent
Stohrer

(10) Patent No.: US 6,232,492 B1
(45) Date of Patent: May 15, 2001

(54) PROCESS FOR THE PREPARATION OF N-ARYL-N-HYDROXAMIDES

(75) Inventor: Juergen Stohrer, Pullach (DE)

(73) Assignee: Consortium fur Elektrochemische Industrie GmbH, Müchen (DE)

( * ) Notice: Subject to any disclaimer, the term of this patent is extended or adjusted under 35 U.S.C. 154(b) by 0 days.

(21) Appl. No.: 09/380,170

(22) PCT Filed: Feb. 26, 1998

(86) PCT No.: PCT/EP98/01084

§ 371 Date: Aug. 25, 1999

§ 102(e) Date: Aug. 25, 1999

(87) PCT Pub. No.: WO98/38159

PCT Pub. Date: Sep. 3, 1998

(30) Foreign Application Priority Data

Feb. 27, 1997 (DE) ................................................ 197 07 969

(51) Int. Cl.[7] ........................ C07C 259/06; C07C 239/08
(52) U.S. Cl. ........................ 560/312; 560/129; 564/161; 564/201

(58) Field of Search ...................................... 560/312, 129; 564/161, 201

(56) References Cited

PUBLICATIONS

Matlin, Stephen A.; Sammes, Peter G.; Upton, Roger M.; J. Chem. Soc., Perkin Trans 1 (1979), (10), pp. 2481–2487.

I.C. Calder, P.J. Williams, J. Chem. Soc. Chem. Comm. (1972), pp. 891–892.

Kato et al, Chem. Pharm. Bul., vol 24(7), pp 1544–1551, 1976.*

Kettrup et al, Talanta, vol. 26, pp 303–307, 1979.*

* cited by examiner

*Primary Examiner*—Shailendra Kumar
(74) *Attorney, Agent, or Firm*—Brooks & Kushman P.C.

(57) ABSTRACT

The invention relates to a method for preparing n-aryl-n-hydroxamides, whereby arylhydroxamines are reacted with ketones to n-aryl-n-hydroxamides, without using acyloxindoles-generating solvents.

14 Claims, No Drawings

PROCESS FOR THE PREPARATION OF N-ARYL-N-HYDROXAMIDES

This application is a 371 of PCT/EP98/01084, filed Feb. 26, 1998.

TECHNICAL FIELD

The invention relates to a process for the preparation of N-aryl-N-hydroxamides.

DESCRIPTION OF THE RELATED ART

Processes for the preparation of N-aryl-N-hydroxamides from the corresponding N-arylhydroxylamines are known. In the synthesis described by Matlin, Stephen A.; Sammes, Peter G.; Upton, Roger M. in J. Chem. Soc., Perkin Trans. 1 (1979), (10), 2481–7, N-arylamides are reacted with suitable silylation agents, such as, for example, hexamethyldisilazane, to give N-trimethylsilyl-N-arylamides, which are then oxidized using peroxovanadate complexes. The desired products are then released from the resulting vanadium complexes of the N-aryl-N-hydroxamides by leaching with EDTA. Because of the necessary protective groups and the lengthy workup, this process is not cost-effective.

I.C. Calder, P. J. Williams, J. Chem. Soc. Chem. Comm. 1972, 891–892 describe the reaction of aryl-hydroxylamines with ketene in diethyl ether or chloroform. However, the product is isolated only in a very low yield (46%) and is contaminated as a result of a lengthy basic extraction process. If ketene is used in excess, two other products are produced (N,O-diacetylarylhydroxylamine and 1-acetyloxindole). Formation of the second byproduct can only be suppressed by carrying out the reaction at –70° C.

In industrial processes, it is difficult to meter ketene exactly stoichiometrically, which means that the known process for the preparation of N-aryl-N-hydrox-amides inevitably always gives at least two byproducts, which reduce the yield and make product isolation difficult. In addition, N-arylhydroxylamines, which have withdrawing substituents, such as, for example, the nitro, cyano or halogen group, can be reacted with ketenes even when they are used stoichiometrically in a non-selective manner to give N-arylhydroxyamides.

The number of byproducts in the processes described can be reduced only by using extremely low and thus uneconomical temperatures.

Moreover, if it is desired to synthesize N,O-diacylarylhydroxylamines, the known processes always produce byproducts which can only be avoided by working at extremely low and thus uneconomical temperatures.

SUMMARY OF THE INVENTION

The object of the invention was, therefore, to overcome the disadvantages of the prior art and to develop a cost-effective process for the preparation of N-aryl-N-hydroxamides which is characterized by high conversion, high yield and simple product isolation, and which produces as few undesired byproducts as possible.

It was a further object of this invention to develop a cost-effective process for the preparation of N,O-diacylarylhydroxylamines which is characterized by high yields and simple product isolation.

This object is achieved by the process according to the invention.

DETAILED DESCRIPTION OF THE INVENTION

The invention provides a process for the preparation of N-aryl-N-hydroxamides in which arylhydroxylamines (I) are reacted with ketenes (II) to give N-aryl-N-hydroxamides (III), where no solvents which form acyloxindoles are used.

Arylhydroxylamines are prepared, for example, by reducing nitrobenzene using zinc, catalytically using hydrogen or hydrazine or electrochemically (see Houben-Weyl, Volume 10/1, pp. 1091 et seq.).

Preferred arylhydroxylamines are those of the formula I

where Ar is an aryl radical selected from the group consisting of phenyl, biphenyl, naphthyl, pyridyl, pyrimidyl, pyridazinyl, triazinyl, furanyl, thiophenyl, pyrrolyl and thiazolinyl and where this aryl radical may be substituted by one or more, identical or different $R^3$ radicals selected from the group consisting of halogen, hydroxyl, formyl, cyano, carbamoyl, carboxyl, ester or salt of the carboxyl radical, sulfono radical, ester or salt of the sulfono radical, sulfamoyl, nitro, nitroso, amino, phenyl, aryl-$C_1$-$C_5$-alkyl, $C_1$-$C_{12}$-alkyl, $C_1$-$C_5$-alkoxy, $C_1$-$C_{10}$-carbonyl, carbonyl-$C_1$-$C_6$-alkyl, phospho, phosphono, phosphonooxy, ester or salt of the phosphonooxy radical and where carbamoyl, sulfamoyl, amino and phenyl radicals can be unsubstituted or mono- or polysubstituted by an $R^2$ radical, and the aryl-$C_1$-$C_5$-alkyl, $C_1$-$C_{12}$-alkyl, $C_1$-$C_5$-alkoxy, $C_1$-$C_{10}$-carbonyl and carbonyl-$C_1$-$C_6$-alkyl radicals can be saturated or unsaturated, branched or unbranched and can be mono- or polysubstituted with an $R^4$ radical, where the $R^4$ radicals are identical or different and are hydroxyl, formyl, cyano, carboxyl, ester or salt of the carboxyl radical, carbamoyl, sulfono, sulfamoyl, nitro, nitroso, amino, phenyl, $C_1$-$C_5$-alkyl, $C_1$-$C_5$-alkoxy or $C_1$-$C_5$-alkylcarbonyl or two of each of the $R^3$ or $R^4$ radicals can be linked in pairs via a [—$CR^5R^6$—]$_m$ bridge, where m is 0, 1, 2, 3 or 4, and $R^5$ and $R^6$ are identical or different and are as defined for $R^3$, and one or more non-adjacent [—$CR^2R^3$—] groups can be replaced by oxygen, sulphur or an unsubstituted or monosubstituted imino radical, and two adjacent [—$CR^5R^6$—] groups can be replaced by a [—$CR^5$=$CR^6$—] group, and $R^5$ and $R^2$ are identical or different and are hydrogen or a $C_1$-$C_{12}$-alkyl radical.

The ketene used is preferably a ketene of the formula (II)

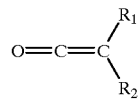

where $R^1$ and $R^2$ are as defined above. The N-aryl-N-hydroxamides (III) have the following formula

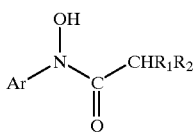

where Ar, $R^1$ and $R^2$ are as defined above.

The process according to the invention is preferably carried out in the presence of solvents or solvent mixtures.

The word solvent does not mean that all reaction components have to be soluble in it. The reaction can also be carried out in a suspension or emulsion of one or more co-reactants.

Examples of suitable solvents in which no acyloxindoles are formed are water, alcohols, such as methanol, ethanol, isopropanol, propanol, butanol, isobutanol, tertiary butanol, hexanol, cyclohexanol, glycol, methoxyethanol, esters, such as methyl acetate, ethyl acetate, butyl acetate, cyclohexyl acetate, ethyl formiate, ethyl butyrate, dimethyl carbonate, acids, such as acetic acid, nitriles, such as acetonitrile, benzonitrile, cyclic ethers, such as tetrahydrofuran, dioxane, amides, such as dimethylformamide, dimethylacetamide, sulphoxides, such as dimethyl sulphoxide, aromatic solvents, such as benzene, toluene, xylene, chlorobenzene, anisole, N,N-dimethylaniline, nitrobenzene, and heteroaromatic compounds, such as pyridine, pyrimidine and mixtures of these solvents. Preferred solvents are water, alcohols, such as methanol, ethanol, isopropanol, propanol, butanol, isobutanol and esters, methanol, ethanol, water and ethyl acetate being particularly preferred.

In ethers, such as diethyl ether and in halogenated hydrocarbons, such as chloroform, acyloxindoles are formed, so these are not used in the process according to the invention.

The process according to the invention is preferably carried out at the pressure of the ambient atmosphere, i.e. about 0.1 MPa (abs.), although it can also be carried out at higher or lower pressures. The process according to the invention is preferably carried out with the exclusion of oxygen.

The process according to the invention is preferably carried out at temperatures of from −30° C. to +100° C., particularly preferably between −10° C. and +50° C.

For the preparation of N-aryl-N-hydroxamides (III), preferably 0.5 to 2.5 mol, particularly preferably 1.0 to 2.2 mol, of ketene of the formula (II) are used per mole of arylhydroxylamine of the formula (I).

For the preparation of N,O-diacylarylhydroxyl-amines (IV), preferably 2.0 to 3.0 mol of ketene of the formula (II) are used per mole of arylhydroxylamine of the formula (I), the N,O-diacylarylhydroxylamines (IV) having the formula (IV)

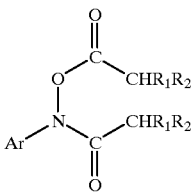

where Ar, $R^1$ and $R^2$ are as defined above.

In the process according to the invention it is possible, even when only N-aryl-N-hydroxamides (III) are to be prepared, that N,O-diacylarylhydroxylamines (IV) are produced as by-product, meaning that to obtain a high yield of N-aryl-N-hydroxamide, N,O-diacylarylhydroxyl-amine (IV) must be converted into the N-aryl-N-hydrox-amide (III).

The conversion of N,O-diacylarylhydroxylamine (IV) into the N-aryl-N-hydroxamide (III) (called cleavage reaction hereinafter) is carried out in the presence of basic compounds. It is not necessary to isolate the N,O-diacylarylhydroxylamine (IV) from the reaction solution for this purpose Basic cleaving compounds which can be used in the process according to the invention are: nitrogen-containing bases selected from the group consisting of ammonia, amines, such as methylamine, ethylamine, cyclohexylamine, ethanolamine, diethanolamine, triethanolamine, morpholine, ethylenediamine, trimethylamine, triethylamine, pyrrolidine, piperidine, aniline, toluidine, phenylenediamine, hydrazine, hydrazides, such as acetic hydrazide, benzoic hydrazide, hydroxylamine, phenylhydroxylamine, methylhydroxylamine, heterocyclic nitrogen bases, such as pyridine, indole, pyrrole, imidazole and pyrimidine, or ionic bases selected from the group consisting of alkali metal and alkaline earth metal hydroxides, alkali metal, ammonium and alkaline earth metal carbonates, alkali metal alkoxides, alkali metal and ammonium salts of carboxylic acids, alkali metal salts of silanols, alkali metal and ammonium salts of thiols, thiophenols and xanthogenic acids, alkali metal and ammonium salts of phenols or other aromatic hydroxyl compounds or mixtures of these bases.

In this reaction, preferably 0.001 to 3 mol, particularly preferably 0.05 to 2 mol, of basic compound are used per mole of arylhydroxylamine of the formula (I).

The conversion of N,O-diacylarylhydroxylamine (IV) into the N-aryl-N-hydroxamide (III) is advantageously carried out in the same apparatus as the first reaction step without isolating the product, although it can also be carried out at a different time in another apparatus.

The conversion is carried out in the presence of the aforementioned solvents and the aforementioned temperatures and pressures.

For applications where the presence of N,O-diacylarylhydroxylamines (IV) is not a problem, the cleavage reaction may be omitted.

The products of the process according to the invention do not have to be isolated from the reaction mixture. If it is desirable to isolate N-aryl-N-hydrox-amides (III), they can be obtained by crystallization or precipitation from the corresponding reaction solutions, or removed from the reaction solutions by extraction and then crystallized.

The reactions according to the invention can also be carried out using crude arylhydroxylamine solutions, i.e. in the presence of nitro- and nitroso aromatic compounds.

EXAMPLES 1.a) N-Acetylphenylhydroxylamine

A ketene/methane gas stream (100 mmol of ketene/h; ketene determination by introduction into NaOH solution and back-titration) is introduced into a solution of 10 g of phenylhydroxylamine in 100 ml of THF via a frit (A=2 cm², pore size 0) at 0C with vigorous stirring. After 1.0 equivalent of ketene has been introduced, the reaction of the phenylhydroxylamine is checked for completeness by TLC and, if necessary, a further 0.05 equivalent of ketene is introduced.

According to HPLC, the product comprises 95% of N-hydroxyacetanilide and 5% of N,O-bisacetylphenylhydroxylamine.

Following complete reaction of the phenylhydroxylamine, the solution is treated with 0.05 equivalent of 25% strength aqueous ammonia under a nitrogen atmosphere and stirred for a further 15 minutes. TLC is used to check whether the cleavage reaction is complete and, if necessary, the cleavage reaction is completed by adding further ammonia.

According to TLC, only N-hydroxyacetanilide is present.

1.b) N-Acetylphenylhydroxylamine

A ketene gas stream (200 mmol of ketene/h; ketene determination by weighing) is introduced into a solution of 10 g of phenylhydroxylamine in 100 ml of ethyl acetate via a frit (A=2 cm$^2$, pore size 0) at 0° C. with vigorous stirring. After 1.0 equivalent of ketene has been introduced, the reaction of the phenylhydroxylamine is checked for completeness by TLC and, if necessary, a further 0.05 equivalent of ketene is introduced.

According to HPLC, the product comprises 95% of N-hydroxyacetanilide and 5% of N,O-bisacetylphenylhydroxylamine.

Following complete reaction of the phenylhydroxylamine, the solution is treated with 0.05 equivalent of 25% strength aqueous ammonia under a nitrogen atmosphere and stirred for a further 15 minutes. TLC is used to check whether the cleavage reaction is complete and, if necessary, the cleavage reaction is completed by adding further ammonia.

According to TLC, only N-hydroxyacetanilide is present.

1.c) N-Acetylphenylhydroxylamine

A ketene/methane gas stream (200 mmol of ketene/h; ketene determination by introduction into NaOH solution and back-titration) is introduced into a solution of 10 g of phenylhydroxylamine in 50 ml of 50% strength aqueous ethanol via a frit (A=2 cm$^2$, pore size 0) at 10° C. with vigorous stirring. After 1.1 equivalent of ketene has been introduced, the reaction of the phenylhydroxylamine is checked for completeness by TLC and, if necessary, a further 0.05 equivalent of ketene is introduced.

According to HPLC, the product comprises 95% of N-hydroxyacetanilide and 5% of N,O-bisacetylphenylhydroxylamine.

Following complete reaction of the phenylhydroxylamine, the solution is treated with 0.05 equivalent of 25% strength aqueous ammonia and stirred for a further 15 minutes. TLC is used to check whether the cleavage reaction is complete and, if necessary, the cleavage reaction is completed by adding further ammonia.

According to TLC, only N-hydroxyacetanilide is present.

1.d) N-Acetylphenylhydroxylamine

Catalytic reduction of nitrobenzene gives a crude solution of 87 g of phenylhydroxylamine, 12 g of aniline and 1 g of azoxybenzene in 90% strength aqueous ethanol.

A ketene gas stream (100 mmol of ketene/h; ketene determination by introduction into NaOH solution and back-titration) is introduced into 50 ml of this solution, corresponding to 8.7 g of phenylhydroxylamine, via a frit (A=2 cm$^2$, pore size 0) at 20° C. with vigorous stirring. After 1.1 equivalent of ketene has been introduced, the reaction of the phenylhydroxylamine is checked for completeness by TLC and, if necessary, a further 0.05 equivalent of ketene is introduced.

Following complete reaction of the phenylhydroxylamine, the solution is treated with 0.05 equivalent of 25% strength aqueous ammonia under a nitrogen atmosphere and stirred for a further 15 minutes. TLC is used to check whether the cleavage reaction is complete and, if necessary, the cleavage reaction is completed by adding further ammonia.

According to HPLC, the product comprises 86% of N-hydroxyacetanilide, 12% of acetanilide and 0.7% of azoxybenzene.

2.) N,O-Diacetylphenylhydroxylamine

A ketene gas stream (100 mmol of ketene/h; ketene determination by introduction into NaOH solution and back-titration) is introduced into a solution of 10 g of phenylhydroxylamine in 100 ml of THF via a frit (A=2 cm$^2$, pore size 0) at 0° C. with vigorous stirring. After 2.0 equivalent of ketene have been introduced, the reaction of the phenylhydroxylamine is checked for completeness by TLC and, if necessary, a further 0.05 equivalent of ketene is introduced.

According to HPLC, only N,O-diacetylphenylhydroxylamine is present. No acetyloxindole was detected.

Following complete reaction of the phenylhydroxylamine, the solution is treated with 1.05 equivalents of 25% strength aqueous ammonia under a nitrogen atmosphere and stirred for a further 30 minutes. TLC is used to check whether the cleavage reaction is complete and, if necessary, the cleavage reaction is completed by adding further ammonia.

According to TLC, only N-hydroxyacetanilide is present.

3.) N-Acetyl-4-cyanophenylhydroxylamine

A ketene gas stream (100 mmol of ketene/h; ketene determination by introduction into NaOH solution and back-titration) is introduced into a solution of 11.6 g of 4-cyanophenylhydroxylamine in 100 ml of THF via a frit (A2 cm$^2$, pore size 0) at 0° C. with vigorous stirring. After 1.0 equivalent of ketene has been introduced, HPLC shows that 45% is N,O-diacetyl-4-cyanophenylhydroxylamine, 8% is N-acetyl-4-cyanophenylhydroxylamine and 2% is O-acetyl-4-cyanophenylhydroxylamine.

After a total of 1.8 equivalents of ketene have been introduced, the reaction of the 4-cyanophenylhydroxylamine is checked for completeness using TLC and, if necessary, a further 0.05 equivalent of ketene is introduced.

Following complete reaction of the 4-cyanophenylhydroxylamine, the solution is treated with 1.05 equivalents of 25% strength aqueous ammonia and stirred for a further 60 minutes. TLC is used to check whether the cleavage reaction is complete and, if necessary, the cleavage reaction is completed by adding further ammonia. The solution is freed from solvent, taken up in methylene chloride and extracted with 50 ml of 10% NaOH. The aqueous phase is separated off and acidified. The resulting precipitate of N-acetyl-4-cyanophenylhydroxylamine is filtered off and dried. (Yield 13.8, 90%).

4.) N-Acetyl-2-methylphenylhydroxylamine

A ketene gas stream (100 mmol of ketene/h; ketene determination by introduction into NaOH solution and back-titration) is introduced into a solution of 10.9 g of 2-methylphenylhydroxylamine in 100 ml of THF via a frit (A=2 cm$^2$, pore size 0) at 0° C. with vigorous stirring. After 1.0 equivalent of ketene has been introduced, the reaction of the 2-methylphenylhydroxylamine is checked for completeness by TLC and, if necessary, a further 0.05 equivalent of ketene is introduced.

According to HPLC, the product comprises 95% of N-acetyl-2-methylphenylhydroxylamine and 5% of N,O-bisacetyl - 2 -methylphenylhydroxyl amine.

Following complete reaction of the 2-methylphenylhydroxylamine, the solution is treated with 0.05 equivalent of 25% strength aqueous ammonia under a nitrogen atmosphere and stirred for a further 15 minutes. TLC is used to check whether the cleavage reaction is complete and, if necessary, the cleavage reaction is completed by adding further ammonia.

According to TLC, only N-acetyl-2-methylphenylhydroxylamine is present.

5.) N-Isobutyrylphenylhydroxylamine

A dimethyl ketene gas stream (100 mmol of dimethyl ketene/h; determination by introduction into NaOH solution and back-titration) is introduced into a solution of 10 g of phenylhydroxylamine in 100 ml of THF via a frit (A=2 cm$^2$, pore size 0) at 0° C. with vigorous stirring. After 1.0 equivalent of dimethyl ketene has been introduced, the reaction of the phenylhydroxylamine is checked for completeness by TLC and, if necessary, a further 0.05 equivalent of dimethyl ketene is introduced.

Following complete reaction of the phenylhydroxylamine, the solution is treated with 0.05 equivalent of 25% strength aqueous ammonia under a nitrogen atmosphere and stirred for a further 60 minutes. TLC is used to check whether the cleavage reaction is complete and, if necessary, the cleavage reaction is completed by adding further ammonia.

According to HPLC, only N-hydroxyisobutyryl-anilide is present.

What is claimed is:

1. A process for the preparation of N-aryl-N-hydroxamides, comprising reacting arylhydroxylamine (I) with a ketene (II) to give N-aryl-N-hydroxamide (III), wherein solvents which form acyloxindoles are not used.

2. The process of claim 1, further comprising reacting at least a portion of said N-aryl-N-hydroxamide (III) with a ketene to give N,O-diacylarylhydroxylamine (IV).

3. The process of claim 1, wherein the arylhydroxylamine used is an arylhydroxylamine of the formula (I):

(I)

where Ar is an aromatic radical.

4. The process of claim 2, wherein the arylhydroxylamine used is an arylhydroxylamine of the formula (I):

(I)

where Ar is an aromatic radical.

5. The process of claim 1, wherein the ketene used is a ketene of the formula (II):

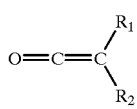

(II)

where $R^1$ and $R^2$ are identical or different and are hydrogen or a $C_1$–$C_{12}$-alkyl radical.

6. The process of claim 2, wherein the ketene used is a ketene of the formula (II):

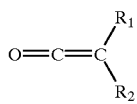

(II)

where $R^1$ and $R^2$ are identical or different and are hydrogen or a $C_1$–$C_{12}$-alkyl radical.

7. The process of claim 3, wherein the ketene used is a ketene of the formula (II):

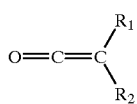

(II)

where $R^1$ and $R^2$ are identical or different and are hydrogen or a $C_1$–$C_{12}$-alkyl radical.

8. The process of claim 4, wherein the ketene used is a ketene of the formula (II):

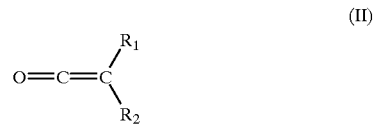

(II)

where $R^1$ and $R^2$ are identical or different and are hydrogen or a $C_1$–$C_{12}$-alkyl radical.

9. The process of claim 1, wherein the N,O-diacylarylhydroxylamine (IV) is selectively cleaved using basic compounds to give N-aryl-N-hydroxamide (III).

10. The process of claim 2, wherein the N,O-diacylarylhydroxylamine (IV) is selectively cleaved using basic compounds to give N-aryl-N-hydroxamide (III).

11. The process of claim 3, wherein the N,O-diacylarylhydroxylamine (IV) is selectively cleaved using basic compounds to give N-aryl-N-hydroxamide (III).

12. The process of claim 5, wherein the N,O-diacylarylhydroxylamine (IV) is selectively cleaved using basic compounds to give N-aryl-N-hydroxamide (III).

13. A process for the preparation of an N-aryl-N-hydroxyamide, said process comprising reacting an N-arylhydroxylamine of the formula (I):

(I)

with a ketene of the formula (II):

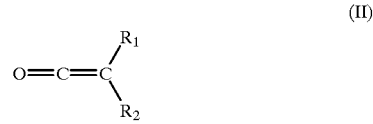

(II)

where $R^1$ and $R^2$ are identical or different $C_1$–$C_{12}$ alkyl groups, in the presence of a solvent which does not promote formation of acyloxindoles to form a reaction mixture containing said N-aryl-N-hydroxamide and N,O-diacylarylhydroxylamine (IV):

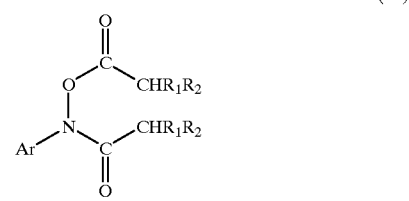

(IV)

and cleaving said N,O-diacylarylhydroxylamine with base to yield N-aryl-N-hydroxamide.

14. The process of claim 13, wherein more than one arylhydroxylamine, more than one ketene, or both more than one arylhydroxylamine and more than one ketene are used.

* * * * *